United States Patent
Lorenzi et al.

(10) Patent No.: US 7,138,246 B2
(45) Date of Patent: Nov. 21, 2006

(54) METHODS FOR IDENTIFYING OR SCREENING FOR AGENTS THAT MODULATE 17β-HSD3

(75) Inventors: Matthew V. Lorenzi, Philadelphia, PA (US); Thomas Spires, Monroe, NJ (US); Dan You, Cranbury, NJ (US); Roberto Weinmann, Princeton, NJ (US); Marco Gottardis, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/068,606

(22) Filed: Feb. 28, 2005

(65) Prior Publication Data

US 2005/0191707 A1    Sep. 1, 2005

Related U.S. Application Data

(60) Provisional application No. 60/620,783, filed on Oct. 21, 2004, provisional application No. 60/620,705, filed on Oct. 21, 2004, provisional application No. 60/549,045, filed on Mar. 1, 2004, provisional application No. 60/548,851, filed on Mar. 1, 2004.

(51) Int. Cl.
*G01N 33/53* (2006.01)
*G01N 33/567* (2006.01)

(52) U.S. Cl. .................. 435/7.1; 435/7.2; 435/7.21; 436/63; 436/86; 436/89; 436/501; 436/518; 530/300; 530/350; 530/387.9

(58) Field of Classification Search ............. 435/7.1, 435/7.2, 7.21; 436/63, 86, 89, 501, 518; 530/300, 350, 387.9
See application file for complete search history.

(56) References Cited

FOREIGN PATENT DOCUMENTS

WO    WO99/46279    9/1999
WO    WO03/022835   3/2003

OTHER PUBLICATIONS

Fiet et al. (Clinical Chemistry 40(12) 2296-2305, 1994).*

Geissler et al., "Male Pseudohermaphroditism Caused by Mutations of Testicular 17β-Hydroxysteroid Dehydrogenase 3", Nat. Gen., vol. 7, pp. 34-39 (1994).
Gheiler et al., "Current Concepts in Androgen Deprivation Therapy—Is There a 'best' Endocrine Treatment?", World J. Urol., vol. 18, pp. 190-193 (2000).
Inano et al., "Testicular 17β-Hydroxysteroid Dehydrogenase: Molecular Properties and Reaction Mechanism", Steroids, vol. 48, pp. 1-26 (1986).
Labrie, "At the Cutting Edge—Intracrinology", Mol. Cell. Endocrinol. vol. 78, pp. C113-C118 (1991).
Labrie et al., "History of LHRH Agonist Combination Therapy in Prostate Cancer", Endocr.-Relat. Cancer, vol. 3, pp. 243-278 (1996).
Liu et al., "Androgens Regulate Proliferation of Human Prostate Cancer Cells in Culture by Increasing Transforming Growth Factor-α (TGF-α) and Epidermal Growth Factor (EGF)/TGF-α Receptor" J. Clin. Endocrinol, vol. 77, pp. 1472-1478 (1993).
Luu-The et al., "Characteristics of Human Types 1, 2 and 3 17β-Hydroxysteroid Dehydrogenase Activities: Oxidation/Reduction and Inhibition", J. Steroid Biochem. Molec. Biol., vol. 55, No. 5/6, pp. 581-587 (1995).
Maltais, R. et al., "Synthesis and Optimization of a New Family of Type 3 17β-Hydroxysteroid Dehydrogenase Inhibotors by Parallel Liquid Phase Chemistry", J. Med. Chem., vol. 45, pp. 640-653 (2002).
Pittaway, "Inhibition of Testosterone Synthesis in the Canine Testis In Vitro", Contraception, vol. 27, No. 4, pp. 431-436 (1983).
Simard et al., "Comparison of In Vitro Effects of the Pure Antiandrogens OH-Flutamide, Casodex and Nilutamide on Androgen-Sensitive Parameters", J. Urol., vol. 49, pp. 580-586 (1997).
Van Weerden et al., "Effects of Low Testosterone Levels and of Adrenal Androgens on Growth of Prostate Tumor Models in Nude Mice", J. Steroid Biochem. Mol. Biol., vol. 37, No. 6, pp. 903-907 (1990).

* cited by examiner

*Primary Examiner*—Long V. Le
*Assistant Examiner*—Lisa Cook
(74) *Attorney, Agent, or Firm*—Paul D. Golian

(57) ABSTRACT

Methods for determining whether a test agent inhibits a 17β-HSD3, the methods comprising: obtaining a recombinant host cell that expresses the 17β-HSD3; obtaining a reaction mixture comprising the 17β-HSD3, androstenedione, and the test agent; measuring the amount of testosterone in the reaction mixture by a scintillation proximity assay (SPA) using SPA beads conjugated with a testosterone-specific antibody, wherein when the amount of testosterone is lower in the presence of a test agent than in the absence of the test agent, the test agent is identified as an inhibitor of the 17β-HSD3.

3 Claims, 15 Drawing Sheets

18β-glycyrrhetinic acid

1,4-androstadiene-1,6,17-trione

| R₁ | R₂ | Enzyme IC₅₀ | Cellular IC₅₀ |
|---|---|---|---|
|  | OPh | 60 | 300 |
|  | OPh | 40 | 710 |
|  | OPh | 1 | 1,200 |
|  | H | 170 | 1,600 |
|  | H | 6,300 | >10,000 |

2-[(3-chloro-4-hydroxybenzoyl)amino]-N-[2-(2-methoxyphenyl)ethyl]-5-phenoxybenzamide (μM)

METHODS FOR IDENTIFYING OR SCREENING FOR AGENTS THAT MODULATE 17β-HSD3

This application claims the benefit of U.S. Provisional Application No. 60/548,851 filed Mar. 1, 2004, U.S. Provisional Application No. 60/549,045 filed Mar. 1, 2004, U.S. Provisional Application No. 60/620,705 filed Oct. 21, 2004, and U.S. Provisional Application No. 60/620,783 filed Oct. 21, 2004, whose contents are hereby incorporated by reference.

BACKGROUND OF THE INVENTION

Prostate cancer (PCa) is the most common malignancy among men, and the inhibition of androgen biosynthesis and its action on its cognate receptors is critical to the therapeutic management of the disease. The biosynthesis of androgens is controlled in the central nervous system (CNS), but also directly in peripheral target tissues. In the CNS, lutenizing hormone release hormone (LHRH) acts on the pituitary to increase lutenizing hormone (LH) production which acts on the testis to increase androgen synthesis. In peripheral tissues, active androgens such as testosterone can also be synthesized directly in target tissues through the conversion of inactive precursors which are present at high levels in the circulation. Current therapies for the hormonal control of PCa counteract CNS control mechanisms through LHRH modulation and/or directly through androgen receptor (AR) antagonism at the site of action to inhibit the growth of hormone-sensitive PCa cells. Although receptor antagonists and LHRH analogues have proven of significant benefit in the treatment of PCa, the enzymes involved in the regulation of local target tissue androgen biosynthesis could also be important points of therapeutic intervention given their ability to regulate both centrally- and peripherally-controlled androgen biosynthesis.

Dihydroepiandrostenedione (DHEA) and androstenedione (AdT) are the major precursors of active sex steroid hormones and are present at high levels in the circulation through production by the adrenal gland. It has been estimated that the levels of DHEA and AdT are in 100–500 fold excess to that of testosterone, which represents a large depot of inactive precursor for conversion to active hormone within target tissues. The enzymes that mediate the last steps in the conversion of inactive to active sex steroids in peripheral target tissues are the 17β- hydroxysteroid dehydrogenases (17β-HSDs), members of the short-chain alcohol dehydrogenase family. At present, nine different human 17β-HSDs have been identified and substrate preferences characterized. This group of related enzymes displays unique patterns of adult tissue distribution and distinct substrate preferences suggesting the evolution of precise control mechanisms on the intracellular production of sex steroid hormones at the local tissue level. Given their key role in catalyzing the formation of active estradiol and testosterone in key target tissues of hormone action, the 17β-HSDs have been considered as potential molecular targets for pharmacological modulation for the treatment of breast and prostate cancers.

Although surgical castration results in a >90% decrease in serum testosterone, levels of testosterone in target tissues such as the prostate are only diminished by ~50% indicating that significant local active hormone synthesis occurs in the absence of a gonadal source. A candidate enzyme for mediating this extragonadal production of active hormone is 17β-HSD3 which has been characterized for its catalysis of the reduction of androstenedione to testosterone (FIG. 1). 17β-HSD3 is expressed in peripheral tissues which are the site of the testosterone action in normal individuals, including at high levels in the seminal vesicles and testes, but has also been shown to be present in prostate tissue. Further, a variety of inactivating mutations have been reported in 17β-HSD3 at a high frequency in a male pseudohermaphroditism syndrome which results in decreased serum testosterone levels and the impairment of the sexual differentiation of the male internal reproductive organs, such as the seminal vesicles and prostate, suggesting that 17β-HSD3 participates in both central and peripheral testosterone synthesis.

17β-hydroxysteroid dehydrogenase 3 (17β-HSD3) is an essential enzyme in the biosynthesis of testosterone. It catalyzes the reduction of androstenedione, a weakly active androgen produced by the adrenal glands, to testosterone (FIG. 1). (Inano et al., Steroids, 48, 1–26, (1986) and Luu-The et al., J. Steroid Biochem. Mol. Biol., 55, 581–587 (1995)) 17β-HSD3 is expressed predominately in the adult testes and to a lesser extent in seminal vesicles and prostate tissue, an expression pattern consistent with an enzyme involved in both gonadal and peripheral target tissue androgen biosynthesis. 17β-HSD3 is responsible for the synthesis of about 60% of all active androgens in men. (Labrie, Mol. Cell. Endocrinol. 78, C113–C118 (1991)) The development and progression of hormone sensitive diseases, e.g., prostate cancer, is stimulated by androgens such as testosterone. Inhibition of 17β-HSD3 therefore provides a novel means to disrupt testosterone biosynthesis for the treatment of androgen-associated diseases. (Van Weerden et al., J. Steroid Biochem. Mol. Biol., 20, 903–907 (1990) and Liu et al., J. Clin. Endocrinol., 77, 1472–1478 (1993)) Current pharmacological treatments to prevent androgen action in androgen-associated diseases such as prostate cancer are centered on the combined use of luteinizing hormone releasing hormone (LHRH) analogues with androgen receptor antagonists ("anti-androgens"). (Labrie et al., Endocr.-Relat. Cancer, 3, 243–278 (1996); Gheiler et al., World J. Urol., 18, 190–193 (2000); Simard et al., J. Urol., 49, 580–586 (1997)) LHRH analogues interfere with central nervous system feedback mechanisms to suppress testosterone biosynthesis in the testes to produce chemical castration. However, it is estimated that up to 50% of testosterone levels remain within prostate tissue following chemical or surgical castration indicating the existence of alternate routes of testosterone biosynthesis independent of the testes. Anti-androgens are used to block the action of this remaining testosterone in prostate cancer cells by antagonizing hormone function at the level of receptor binding. Although the combined use of LHRH analogues with anti-androgens has shown success in the management of prostate cancer, these responses are largely restricted to advanced metastatic disease. Further, patients receiving these treatments ultimately become refractory and progress to a more aggressive, hormone-independent state for which there is no effective therapy.

Inhibitors of 17β-HSD3 have been described in the art. (Pittaway, Contraception, 27, 431 (1983); Labrie et al., WO99/46279; Maltais et al., J. Med. Chem., 45, 640–653 (2002); Guzi et al., WO03/022835).

The role of 17β-HSD3 in both centrally and peripherally controlled testosterone biosynthesis, suggests that 17β-HSD3 inhibitors may be beneficial for the treatment of hormone-sensitive prostate cancers. It would be desirable to have a method to identify or screen for agents that inhibit 17β-HSD3.

SUMMARY OF THE INVENTION

The invention provides methods for identifying or screening for agents that modulate 17β-HSD3. As used herein, modulate refers to the inhibition or activation of the activity of 17β-HSD3.

In one aspect, the invention provides a method for determining whether a test agent inhibits a 17β-HSD3, said method comprising: obtaining a recombinant host cell that expresses said 17β-HSD3; obtaining a reaction mixture comprising said 17β-HSD3, androstenedione, and said test agent; measuring the amount of testosterone in said reaction mixture by a scintillation proximity assay (SPA) using SPA beads conjugated with a testosterone-specific antibody, wherein when the amount of testosterone is lower in the presence of a test agent than in the absence of the test agent, the test agent is identified as an inhibitor of said 17β-HSD3.

In another aspect, the invention provides a method for determining whether a test agent inhibits a 17β-HSD3, said method comprising: obtaining a reaction mixture comprising a recombinantly produced 17β-HSD3 cellular lysate, androstenedione, and said test agent; measuring the amount of testosterone in said reaction mixture by a scintillation proximity assay (SPA) using SPA beads conjugated with a testosterone-specific antibody, wherein when the amount of testosterone is lower in the presence of a test agent than in the absence of the test agent, the test agent is identified as an inhibitor of said 17β-HSD3.

These methods of the invention can also be used to determine whether a test agent activates a 17β-HSD3, wherein when the amount of testosterone is higher in the presence of a test agent than in the absence of the test agent, the test agent is identified as an activator of said 17β-HSD3.

The recombinant host cell can be selected from those host cells having low levels of intrinsic 17β-HSD3 conversion activity. Suitable host cells include, for example, HEK293, BT549, and MDA MB 453 cells.

The recombinant host cell that expresses 17β-HSD3 is, in one aspect, a cellular lysate comprising an accumulation of 17β-HSD3 which is combined with androstenedione and the test agent to form said reaction mixture.

The testosterone-specific antibody includes any antibody that specifically recognizes and binds to testosterone, and does not bind with specificity to androstenedione (AdT), dihydroepiandrostenedione (DHEA), estrone, or estradiol. The testosterone-specific antibody can be, for example, a human, murine, goat, rabbit, or chicken antibody.

The step of obtaining the recombinant host cell can, in one aspect, comprise transfecting said host cell with a polynucleotide comprising a nucleotide sequence that encodes said 17β-HSD3 under conditions such that said host cell produces said 17β-HSD3.

The SPA beads used in the method can be, for example, an anti-mouse IgG-scintillant bead.

The invention also provides a method for identifying a test agent that inhibits a 17β-HSD3, said method comprising: obtaining a recombinant host cell that expresses said 17β-HSD3 and a testosterone-responsive gene promoter that drives expression of a secreted alkaline phosphatase (SEAP) reporter; combining said test agent with said recombinant host cell; and measuring the transcription of said SEAP reporter, wherein when the amount of said SEAP reporter is lower in the presence of a test agent than in the absence of the test agent, the test agent is identified as an inhibitor of said 17β-HSD3. This method of the invention can also be used to determine whether a test agent activates a 17β-HSD3, wherein when the amount of said SEAP reporter is higher in the presence of a test agent than in the absence of the test agent, the test agent is identified as an activator of said 17β-HSD3.

DETAILED DESCRIPTION

Figure 1:
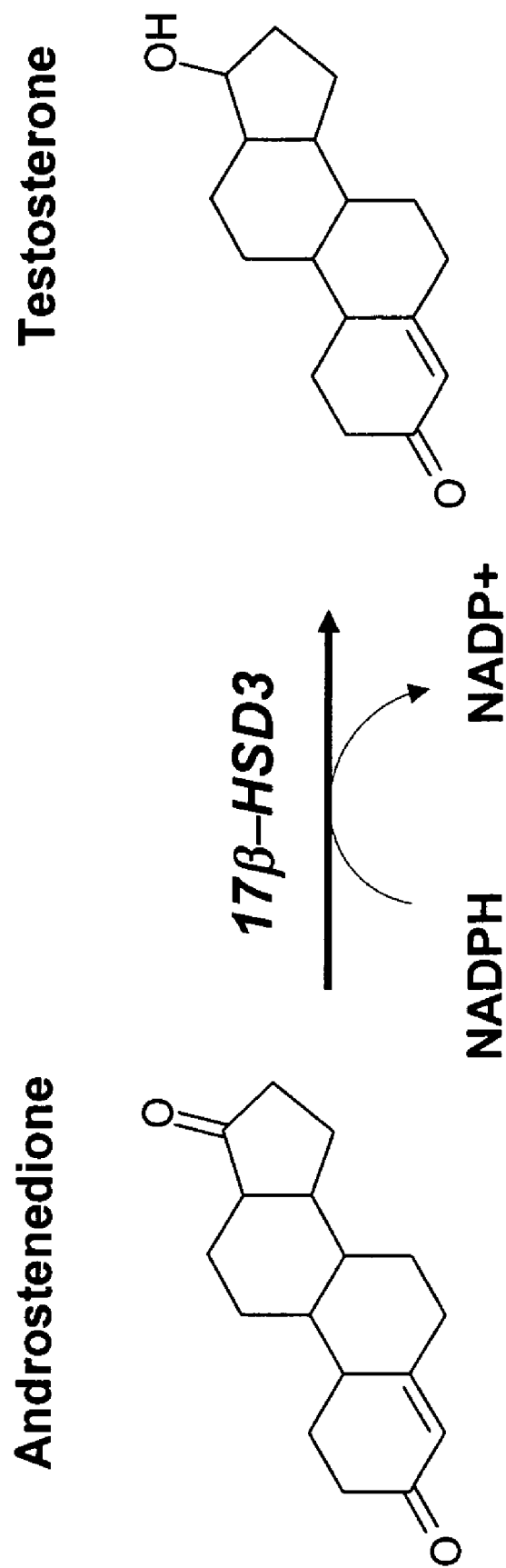
FIG. 1 illustrates the reduction of androstenedione to testosterone catalyzed in a NADPH dependent manner by 17β-HSD3.

The treatment of prostate cancer relies on disrupting the effects of testosterone action either in the central nervous system through lutenizing hormone releasing hormone (LHRH) modulation and/or by direct modulation of androgen receptor (AR) function by receptor antagonists in peripheral target tissues such as prostate and testis. In an effort to evaluate new therapies which could inhibit both central and peripheral testosterone actions, rapid biochemical and cellular screening assays were developed to identify inhibitors of 17β-hydroxysteroid dehydrogenase type III (17β-HSD3), the enzyme catalyzing the conversion of androstenedione to testosterone.

The nucleotide and amino acid sequences for human 17β-HSD3 are provided, for example, in GenBank Accession Nos. NM_000197 (SEQ ID NO:1) and NP_000188 (SEQ ID NO:2).

NM_000197 (SEQ. ID NO:1)

```
   1 tacacagaga gccacggcca gggctgaaac agtctgttga gtgcagccat gggggacgtc
  61 ctggaacagt tcttcatcct cacagggctg ctggtgtgcc tggcctgcct ggcgaagtgc
 121 gtgagattct ccagatgtgt tttactgaac tactggaaag ttttgccaaa gtctttcttg
 181 cggtcaatgg gacagtgggc agtgatcact ggagcaggcg atggaattgg gaaagcgtac
 241 tcgttcgagc tagcaaaacg tggactcaat gttgtcctta ttagccggac gctggaaaaa
 301 ctagaggcca ttgccacaga gatcgagcgg actacaggga ggagtgtgaa gattatacaa
 361 gcagatttta caaagatga catctacgag catattaaag aaaaacttgc aggcttagaa
 421 attggaattt tagtcaacaa tgtcggaatg cttccaaacc ttctcccaag ccatttcctg
 481 aacgcaccgg atgaaatcca gagcctcatc cattgtaaca tcacctccgt agtcaagatg
 541 acacagctaa ttctgaaaca tatggaatca aggcagaaag gtctcatcct gaacatttct
 601 tctgggatag ccctgtttcc ttggcctctc tactccatgt actcagcttc caaggcgttt
 661 gtgtgcgcat tttccaaggc cctgcaagag gaatataaag caaagaagt catcatccag
 721 gtgctgaccc catatgctgt ctcgactgca atgacaaagt atctaaatac aaatgtgata
 781 accaagactg ctgatgagtt tgtcaaagag tcattgaatt atgtcacaat tggaggtgaa
 841 acctgtggct gccttgccca tgaaatcttg gcgggctttc tgagcctgat cccggcctgg
 901 gccttctaca gcggtgcctt ccaaaggctg ctcctgacac actatgtggc atacctgaag
 961 ctcaacacca aggtcaggta gccaggcggt gaggagtcca gcacaacctt ttcctcacca
1021 gtcccatgct ggctgaagag gaccagagga gcagaccagc acttcaacct agtccgctga
1081 agatggaggg ggctggggtc acagaggcat agaatacaca tttttgcca cttt
```

NP_00188 (SEQ. ID NO:2)

```
  1 mgdvleqffi ltgllvclac lakcvrfsrc vllnywkvlp ksflrsmgqw avitgagdgi
 61 gkaysfelak rglnvvlisr tlekleaiat eierttgrsv kiiqadftkd diyehikekl
121 agleigilvn nvgmlpnllp shflnapdei qslihcnits vvkmtqlilk hmesrqkgli
181 lnissgialf pwplysmysa skafvcafsk alqeeykake viiqvltpya vstamtkyln
241 tnvitktade fvkeslnyvt iggetcgcla heilagflsl ipawafysga fqrlllthyv
301 aylklntkvr
```

Several classes of non-steroidal, low molecular weight compounds were identified which potently inhibited 17β-HSD3 enzymatic activity. One of the most potent classes of 17β-HSD3 inhibitors was a series of anthranilamide compounds related to modulators of nuclear hormone receptors. This series of compounds displayed potent inhibition of 17β-HSD3-mediated cellular conversion of androstenedione to testosterone and inhibited the ability of 17β-HSD3-mediated conversion to promote androgen receptor dependent transcription. The identification of potent non-steroidal inhibitors of 17B-HSD3 may be a useful alternative approach for the disruption of testosterone biosynthesis in the treatment of prostate cancer.

EXAMPLES

Material and Methods

Steroids, Chemicals, & Reagents

All radiochemicals ([3H]4-Androstene-3,17-Dione, [3H] Testosterone, [3H]Estradiol, and [3H]Estrone) were purchased from Perkin Elmer Life Sciences. All unlabeled hormones, 18b-Glycyrrhetinic Acid, and silica gel thin layer chromatography (TLC) plates were obtained from Sigma-Aldrich. Scintillation Proximity Assay beads conjugated to anti-mouse IgG were purchased from Amersham Biosciences. The anti-testosterone antibody (mouse anti-testosterone (3-BSA) monoclonal antibody) was obtained from Chemicon International (Catalog Number MAB1236) and the cofactor NADPH was obtained from CalBiochem. All other reagents, unless otherwise stated below, were purchased from VWR Scientific or Sigma-Aldrich.

Cloning and Plasmids

17β-HSD3-pCDNA3

The human 17beta-HSD3 cDNA was received from Steve Andersson (Geissler et al., Nat. Gen., May;7(1):34–39 (1994)). The sequence was then cloned into pcDNA3.1 (Invitrogen) using BamHI and NotI sites. The entire sequence was verified by DNA sequencing and the plasmid was used for transfection into human cancer cell lines as described herein.

PSA-SEAP

A 540 bp region of DNA containing the enhancer and promoter regions of the human PSA (Prostate Specific Antigen) gene was cloned from human cDNA into the pSEAP2-Basic vector (BD Bioscience), just upstream of the SEAP gene using BglII and HindIII. The PSA-SEAP2 gene was specifically regulated through androgen receptor signaling when stimulated by the AR ligands testosterone or dihydrotestosterone and not by the ligands of other Nuclear Hormone Receptors (data not shown). The entire sequence was verified by DNA sequencing and the plasmid was used as described herein. The PSA enhancer/promoter sequence that was cloned into the SEAP vector was:

(SEQ ID NO:3)
gatcttttatgatgacagtagcaatgtatctgtggagctggattctggg ttgggagtgcaaggaaaagaatgtactaaatgccaagacatctatttcag gagcatgaggaataaaagttctagtttctggtctcagagtggtgcaggga tcagggagtctcacaatctcctgagtgctggtgtcttagggcacactggg tcttggagtgcaaaggatctaggcacgtgaggctttgtatgaagaatcgg ggatcgtacccacccctgtttctgtttcatcctgggcatgtctcctctg cctttgtccctagatgaagtctccatgagctacaagggcctggtgcatc cagggtgatctagtaattgcagaacagcaagtgctagctctccctcccct tccacagctctgggtgtgggaggggttgtccagcctccagcagcatggg gagggccttggtcagcctctgggtgccagcagggcaggggcggagtcctg gggaatgaaggttttataggggctcctgggggaggctcccagcccaa.

Cell Culture and Transfections

All cell lines were obtained from American Type Culture Collection (ATCC). Cells were maintained in their appropriate media supplemented with 10% heat inactivated fetal bovine serum (v/v) at 37° C. in 5% $CO_2$. For all cell based assays, the media were supplemented with 5–10% charcoal stripped fetal bovine serum (cFBS) (Hyclone). HEK293 and MDA MB 453 cell lines were transfected with the 17β-HSD3 pcDNA3 construct using lipofectamine (Invitrogen) and stable clones isolated under selective pressure using G418 (Invitrogen). The HEK293/17β-HSD3 clone was chosen based on the highest level of enzymatic activity as determined by both TLC analysis and SPA (data not shown). The MDA MB 453 clone was chosen based on similar criteria using TLC analysis and the cell based reporter assay (data not shown). Stable clones were then maintained in DMEM/10% FBS supplemented with 500 μg/mL of G418.

Enzyme Expression and Isolation

HEK293/17β-HSD3 cells were harvested by scraping or treatment with Cell Dissociation Buffer (Invitrogen) and collected in ice cold Phosphate Buffered Saline (PBS) containing a protease inhibitor cocktail (Complete Tabs, Roche Diagnostics). The cells were then pelleted by centrifugation at 1000 rpm and washed once more in the same buffer. The cells were then resuspended in 2× the cell pellet volume with ice cold lysis buffer (40 mM Tris-HCl pH7.5, 2 mM DTT, 1 mM EDTA, 10% Glycerol (v/v), 0.5% CHAPS (w/v), 1M 1-(3-sulfopropyl)pyridinium hydroxide, Complete Tab(s)) and dounce homogenized on ice. The crude lysate was then incubated on ice for 60 minutes to allow for membrane protein solubilization, followed by centrifugation at 100,000×g for 60 minutes at 4° C. The supernatant was then removed and dialyzed overnight at 4° C. against the enzyme storage buffer (40 mM Tris-HCl pH 7.5, 40 mM KCl, 2 mM DTT, 1 mM EDTA, 20% Glycerol (v/v), Complete Tab(s)). Protein concentration was determined by the Bradford assay, the enzyme was aliquotted, and stored at −80° C. Activity was assessed using the SPA described below.

Scintillation Proximity Assay (SPA)

SPA beads conjugated to anti-mouse IgG were incubated overnight in SPA Bead Buffer (50 mM Tris pH 8.0, 10% Glycerol (v/v)), with anti-Testosterone monoclonal antibody (2 μg antibody per 1 mg of SPA beads) under gentle rotation. The antibody saturated bead complex was then spun down at 500 rpm for 10 minutes at 4° C. and the beads were resuspended in SPA Bead Buffer at a final concentration of 0.5 mg/160 μL. The anti-T/SPA Beads were then stored at 4° C. until needed. Enzymatic assays were conducted in 30 μL total reaction volumes in 96-well white Optiplates (Perkin Elmer). The reaction buffer consisted of 50 mM MES pH 6.0, 2 mM DTT, 0.1% CHAPS, 3 mM NADPH, 10% Glycerol (v/v), 850 nM 4-Androstene-3,17-Dione, and 50 nM [3H]4-Androstene-3,17-Dione (Specific Activity 70–110Ci/mmol). Compounds were diluted such that the final concentration of ethanol and DMSO would not exceed 3% (v/v) and 1% (v/v) respectively, corresponding to concentrations that had little or no effect on enzymatic activity (data not shown). Previously prepared and frozen 17β-HSD3 enzyme was diluted into ice cold buffer containing 50 mM Mes, 40 mM KCl, 2 mM DTT, 1 mM EDTA, and 10% glycerol (v/v) and added last to the reaction mixture. The reaction was allowed to proceed for 60 minutes at room temperature and was stopped by the addition of 10 μL of 0.1N HCl. After the reactions were stopped, an excess of the anti-T/SPA Beads (0.5 mg) were added to each well to a final volume of 200 µL. The plates were sealed and shaken at ~200 rpm on an orbital shaker at room temp for at least 90 minutes or overnight at 4° C. After allowing the beads to settle, the amount of [3H]Testosterone produced in each well was determined by scintillation counting on a Perkin Elmer TopCount instrument and collected as DPMs. The data was then analyzed and percent inhibition and/or IC50 values, based on 10 point serially diluted curves in duplicate or triplicate, were calculated using Microsoft Excel and XLFit programs. For 17β-HSD3 kinetic analysis, the enzymatic reactions were carried out as described above except that a large excess of SPA beads (~10 fold) was used to ensure that all the substrate being produced would be captured. The Km for testosterone was obtained in the presence of 3 mM NADPH and the Km for NADPH was obtained in the presence of 0.9 mM testosterone. Input samples and unbound supernatants, from the enzymatic reactions, were quantitated by scintillation counting to aid in the calculation of bound versus free testosterone produced. Km values were calculated using the Lineweaver-Burke formula and plots where $1/v=(Km+[s])/(Vmax [s])$.

Thin Layer Chromatography (TLC) Analysis

Cells were plated in 24-well tissue culture plates at $5\times10^4$ cells per well in their appropriate media. After allowing the cells to adhere for 24 hours, the media was changed to contain 10% cFBS (charcoal treated FBS) (300 µL) per well and 0.5µ Ci of the radiolabeled hormones were added to each well. After 3 hours, the supernatant was removed and 500 µL of extraction buffer (3 parts Ethyl Acetate: 1 part Acetone) was added to each sample and vortexed extensively. The organic layer was carefully removed and dried down in siliconized 1.5 mL microfuge tubes (National Scientific Supply Co.). 20 µL of the extraction buffer was then used to resolubilize the extracted hormones and spotted onto silica gel TLC plates. The plates were then put into a glass chamber containing 225 mL of running buffer (6 parts Chloroform: 2 parts Ethyl Acetate: 1 part Acetone) and allowed to incubate until the solvent front was approx 1–2 inches from the top of the plate. The plates were removed from the tank and allowed to air dry. Once dry, the plates were wrapped in plastic and put into a film cassette with a Fujifilm BAS Imaging Screen designed for tritium detection and exposures were allowed to proceed overnight. The BAS screens were then read using a Fujifilm PhosphoImager FLA-2000 and spots were quantitated using the Fujifilm MacBas imaging/densitometry program.

17β-HSD3 SEAP Assay

Cultured MDA MB 453/17β-HSD3 cells were trypsinized, spun at 1000 rpm for 10 minutes, and resuspended in DMEM/10% cFBS supplemented with 5 mM BES at a concentration of $4\times10^7$ cells per mL. The cells (aliquots of $1\times10^7$ cells) were then transiently transfected with 3 µg of the PSA-SEAP construct by electroporation at 0.22 kVolts and 960 µFD with a time constant of 44–46 seconds. After a short recovery period, the cells were spun down and resuspended in DMEM/10% cFBS and plated into 96-well tissue culture plates ($5\times10^5$ cells per well in 50 µL). After overnight adherence, the compounds were diluted in DMEM/10% and cFBS was added to the cells. 24 hours later, the medium was removed, fresh media containing the compounds was added in the presence of 10 nM Androstenedione, and this mixture was allowed to incubate for 24 hours. 25 µL of the culture supernatant was then removed and plated into 96-well black Optiplates (Perkin Elmer) for SEAP measurement as described by the reagent manufacturer (Tropix). Briefly, the supernatant was heat inactivated at 65° C. for 30 minutes and then allowed to cool to room temperature. Assay buffer (25 µL, Tropix) was then added and allowed to mix for 5 minutes followed by the addition of the Reaction buffer (25 µL, Tropix) and the plates were then incubated for 20 minutes in the dark. Plates were then read using a Packard Instruments TopCount with luminescent detection and signal was captured for 10 seconds per well and photon emission (cps) was averaged. A standard MTS assay (Promega) as described by the manufacturer, was performed in parallel to normalize the data based on cell numbers. Data analysis including percent inhibition and IC50 determination, based on 10 point serially diluted curves in duplicate, was then performed using Microsoft Excel and XLFit.

Results

17β-HSD3 Scintillation Proximity Assay (SPA)

The reduction of androstenedione to testosterone occurs in the testes and in peripheral target tissues of testosterone action such as the seminal vesicles and prostate. This reaction has been shown to be catalyzed in a NADPH dependent manner by 17β-HSD3 (FIG. 1) or by 17β-HSD5, a evolutionarily distinct dehydrogenase of the aldo-keto reductase family. Given the expression of 17β-HSD3 in both testes and prostate tissue and inactivating mutations observed in a male pseudohermaphrodite syndrome with testosterone biosynthesis defects, it was reasoned that modulation of 17β-HSD3 activity would be useful for treating androgen-dependent disorders such as hormone-sensitive prostate cancer.

Figure 2A:
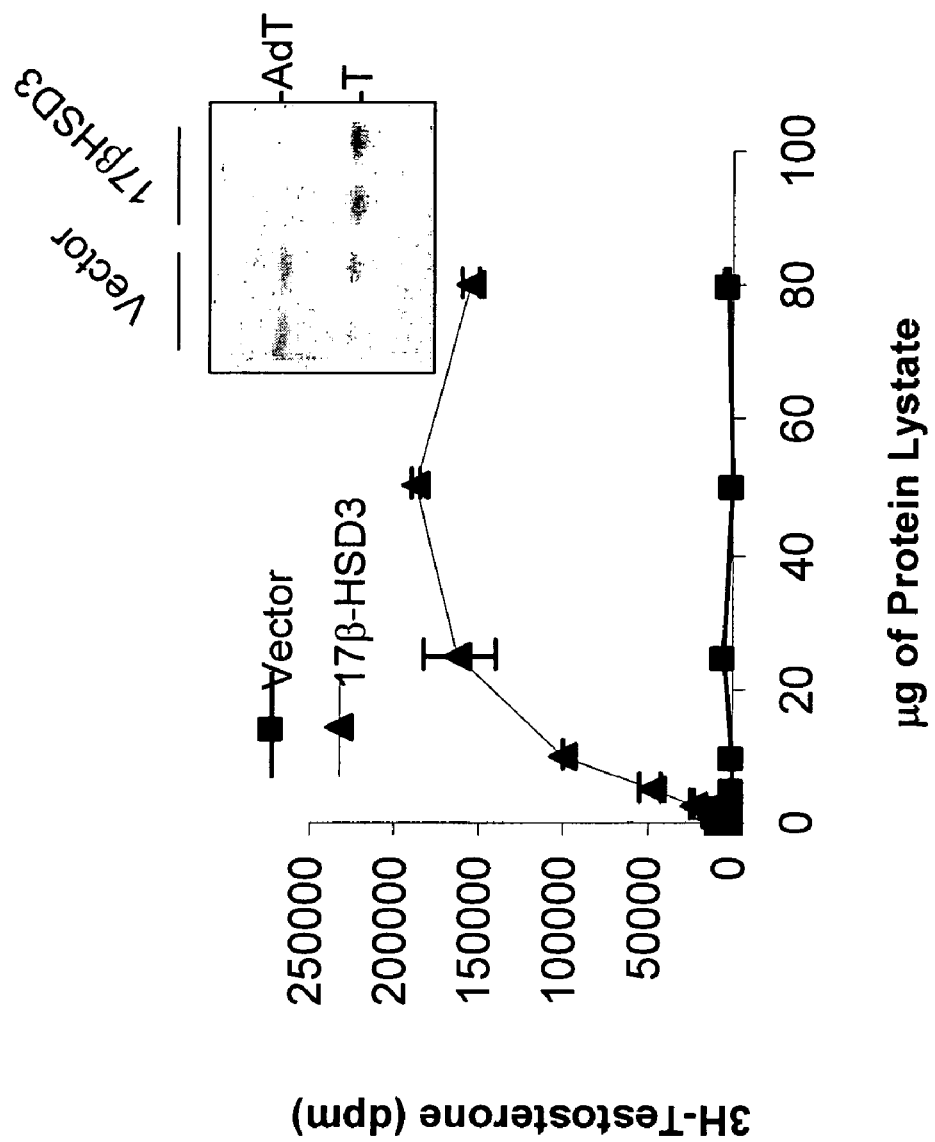
FIG. 2 (FIGS. 2A and 2B) illustrates the enzymatic properties of 17β-HSD3. Transfectants of the human kidney tumor cell line HEK293 were engineered to stably express human 17β-HSD3. 17β-HSD3-HEK293 transfectants incubated with radioactive androstenedione displayed pronounced testosterone conversion activity compared to vector-transfectant controls (FIG. 2A, inset). Microsomal preparations of 17β-HSD3-HEK293 cells were used to develop a scintillation proximity assay (SPA) which monitored the biochemical conversion of $\{^3H\}$-androstenedione to $\{^3H\}$-testosterone. Kinetic analysis of 17β-HSD3 displaying a 0.92 µM Km of the enzyme for androstenedione is shown in FIG. 2B.

To this end, a scintillation proximity assay (SPA) amenable for high throughput compound screening was designed using a testosterone-specific antibody. This antibody efficiently recognized testosterone and dihydrotestosterone (DHT) but not androstenedione (AdT), dihydroepiandrostenedione (DHEA), estrone, or estradiol (data not shown). A SPA was designed using this anti-testosterone antibody to monitor the production of {3H}-testosterone from {3H}-androstenedione in the presence of NADPH and 17β-HSD3. The amount of {3H}-testosterone produced in the reaction was quantified by the anti-testosterone monoclonal antibody precomplexed to an anti-mouse IgG-scintillant bead. As human 17β-HSD3 is predicted to encode a protein with several membrane-spanning regions and has been shown to be associated with microsomes, stable transfectants of 17β-HSD3 or vector were engineered in HEK293 cells and microsomal preparations were isolated as the source of 17β-HSD3 enzyme. Vector transfectants of HEK293 displayed a low level of androstenedione to testosterone conversion activity when incubated with {3H}-androstenedione for 24 hours (FIG. 2A, inset). In contrast, stable 17β-HSD3 transfectants incubated with {3H}-androstenedione under the same conditions displayed constitutive conversion to testosterone, indicating that these cells could be used as a source of active human 17β-HSD3 enzyme. Microsomal preparations were prepared from both vector and 17β-HSD3 transfectants and tested in the SPA format for testosterone conversion activity (FIG. 2A). Microsomal preparations from vector-transfectants did not show any appreciable testosterone production using up to 80 µg of protein in the reaction. In contrast, the partially-purified 17β-HSD3 enzyme preparation from HEK29 transfectants displayed a robust androstenedione to testosterone conversion activity with the reaction saturating at a ~20-fold induction level between 50–80 µg protein/reaction. Significant 17β-HSD3-mediated testosterone conversion activity was also observed within a linear range using lower levels of protein ranging from 100 ng to 25 µg. The level of increase of 17β-HSD3 reductive activity at 5 µg, 10 µg, and 25 µg was 6-fold, 13-fold or 21-fold, respectively, indicating that the 17β-HSD3 SPA was robust and dose-proportional across a wide range of protein concentration.

Figure 2B:
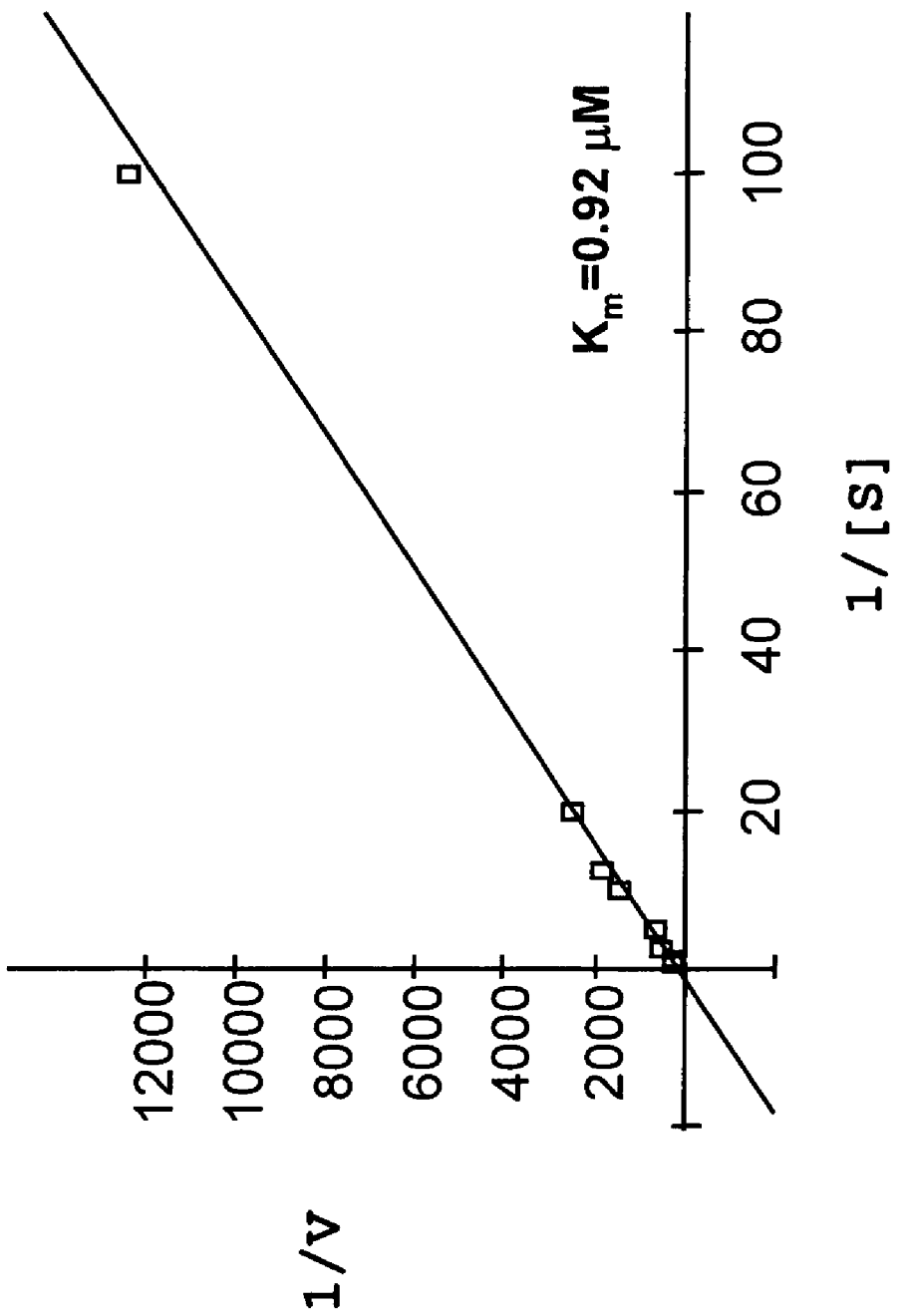

To determine the optimal concentration of substrate to use for the identification of compound (i.e., test agent) inhibitors of 17β-HSD3, kinetic analysis was performed for androstenedione, the steroid substrate of 17β-HSD3. Testosterone production was determined over serial dilutions comprising 0.01 to 10 µM input androstenedione. Under these conditions, a $K_m$ for androstenedione was determined to be 0.92 µM (FIG. 2B) which was consistent with a previously published value of 0.72 µM on human 17β-HSD3 prepared from testes microsomal fractionation. $K_m$ values for NADPH, the co-factor of the 17β-HSD3 reaction, were also determined. The results were presented as Lineweaver-Burke plots and the $K_m$ for NADPH was calculated as 30 µM for 17β-HSD3. To ensure the likelihood of identifying inhibitors of the androstenedione over the NADPH co-factor site, assays were performed at the $K_m$ for androstenedione (0.9 RAM) and at 3 mM NADPH, a concentration of co-factor in ~100-fold excess of the 17β-HSD3 NADPH $K_m$, for the identification of small molecule inhibitors.

Inhibition of 17β-HSD3 by 18β-Glycyrrhetinic Acid

Figure 3A:
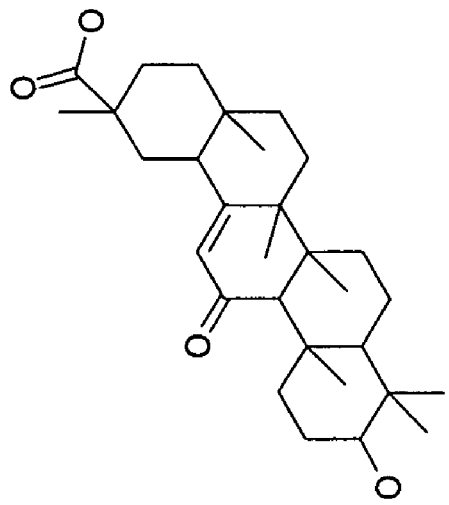
FIG. 3 (FIGS. 3A and 3B) illustrates the inhibition of 17β-HSD3 by 18β-glycyrrhetinic acid, 1,4-androstadiene-1,6,17-trione, and hydroxyflutamide.
Figure 3A:
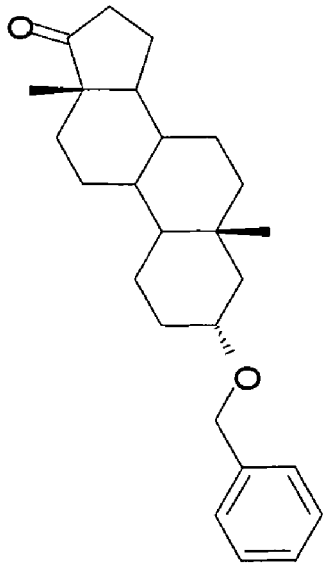
Figure 3B:
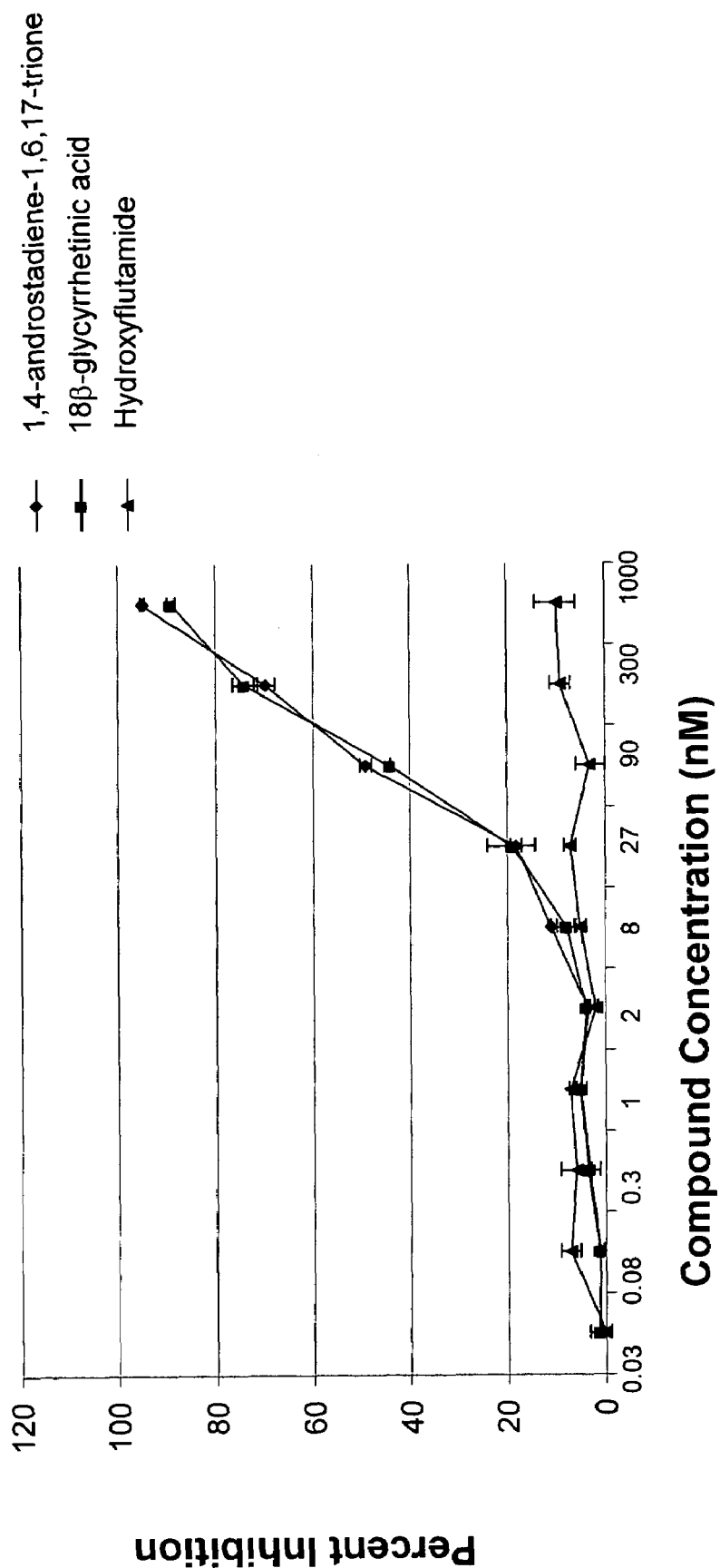

18β-glycyrrhetinic acid (FIG. 3A) is a natural product present in licorice and previously found to inhibit enzymes involved in sex steroid metabolism such as 17β-HSD5 and 11β-HSD. Given that 18β-glycyrrhetinic acid could inhibit the reductive reaction of 17β-HSD5 to convert androstenedione to testosterone, its potential inhibitory activity on 17β-HSD3 was examined. In addition, 1,4-androstadiene-1, 6,17-trione, a structural derivative of androstenedione (FIG. 3A) and shown previously to inhibit 17β-HSD3, was also examined. In the 17β-HSD3 SPA, both 18β-glycyrrhetinic acid and 1,4-androstadiene-1,6,17-trione displayed potent inhibitory activity of 17β-HSD3 (FIG. 3B). In contrast, hydroxyflutamide, a direct androgen receptor antagonist, did not display 17β-HSD3 inhibitory activity. These results indicate that the 17β-HSD3 SPA is a sensitive method for the identification of sub-micromolar enzymatic inhibitors.

Endogenous Steroid Conversion Activity of Breast and Prostate Tumor Cell Lines

Figure 4A:
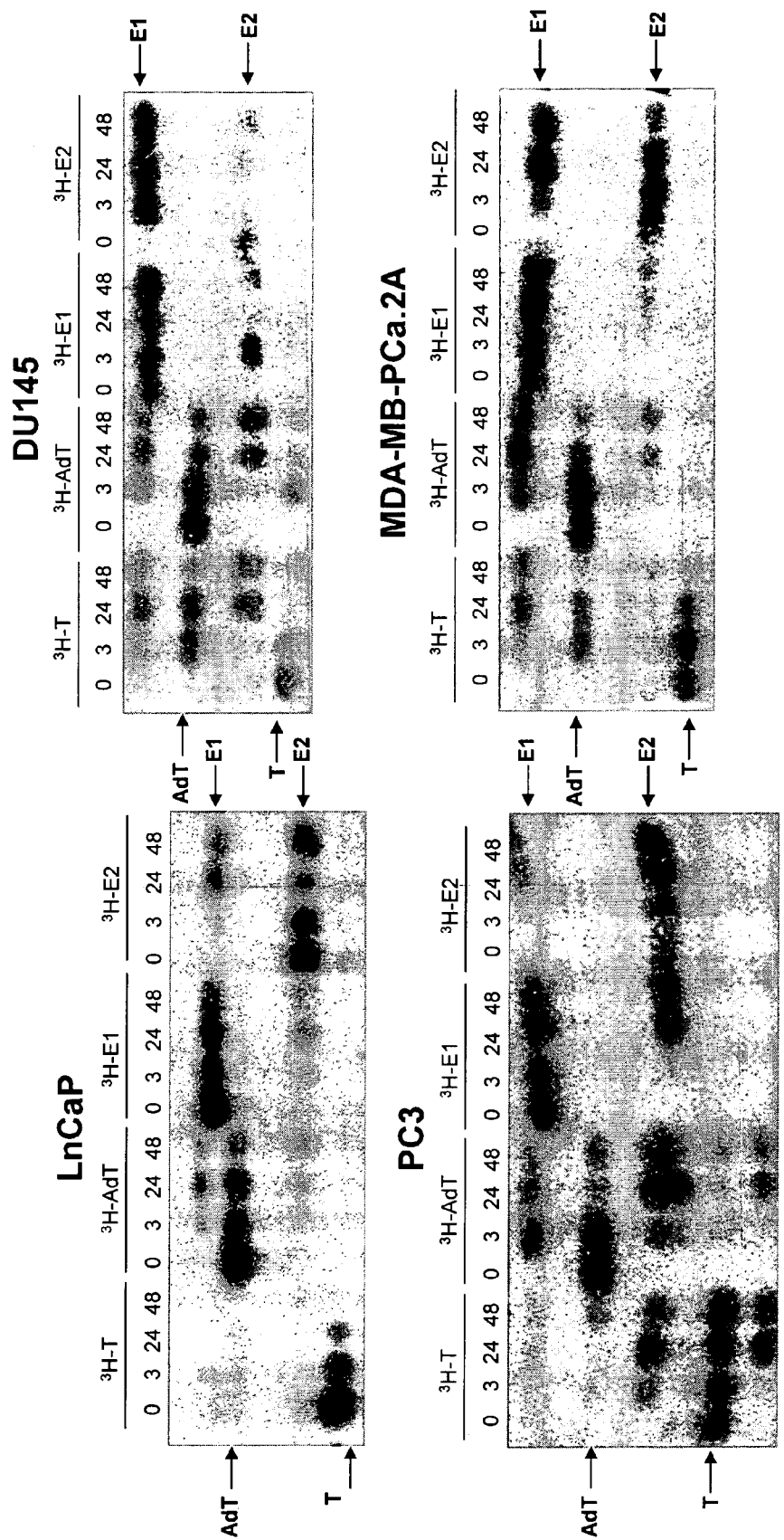
FIG. 4 (FIGS. 4A–4B) illustrates the characterization of prostate and breast tumor cell lines for sex steroid conversion activity. Prostate (FIG. 4A) or breast (FIG. 4B) human tumor cell lines were characterized for their ability to convert estrone (E), estradiol (E2), androstenedione (AdT), or testosterone (T). Cells were incubated with the indicated radioactive hormones over 48 hours and resulting hormone products formed are denoted by arrows.
Figure 4B:
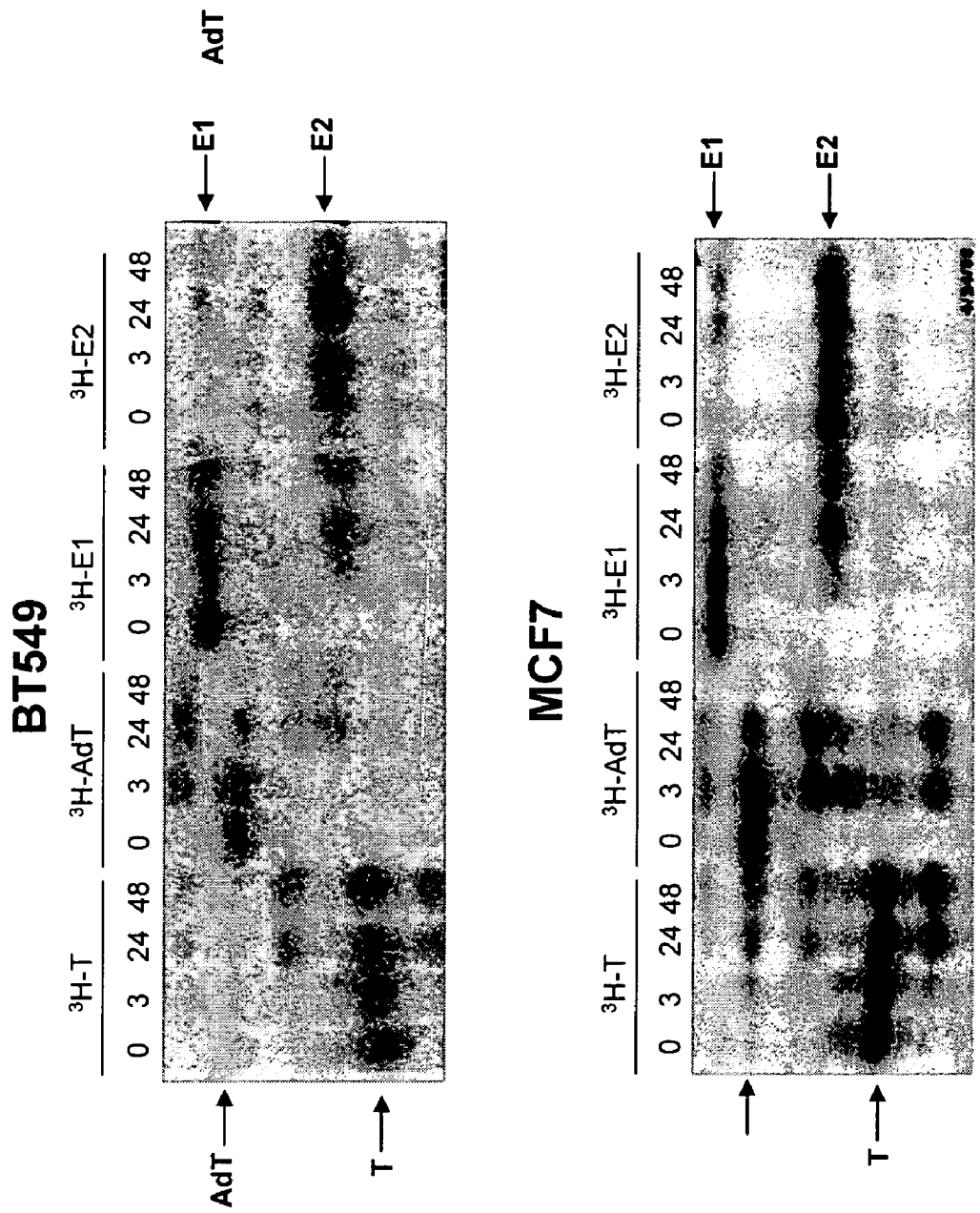

The conversion of steroid precursors to their active counterparts is a mechanism whereby endocrine-responsive tumor cells lines could be altered to promote growth. To evaluate this hypothesis and to characterize the steroid conversion pathways in greater detail, breast and prostate tumor cell lines were incubated with {3H}-testosterone, -androstenedione, -estrone or -estradiol and analyzed for sex steroid production by thin layer chromatography (FIG. 4). Interestingly, prostate cancer cell lines incubated with testosterone displayed conversion back to androstenedione (DU145, MDA-MB-PCa.2A) or estrone (PC3). In addition, incubation with {3H}-estradiol resulted in rapid conversion to estrone in LnCaP, DU145, and MDA-MB-PCa.2A. In contrast, {3H}-androstenedione predominantly was converted to estradiol over time in PC3, MDA-MB-PCa.2A, DU145 and a lesser extent in LnCaP (FIG. 4A). In contrast, breast tumor cells lines did not display oxidative conversion of estradiol but did display similar inactivating conversion of testosterone to estrone (FIG. 4B). These observations suggest a balance of conversion activity shifted toward growth inhibitory estrogenic pathways in these prostate cancer cell lines but not breast cancer cells.

Inhibition of 17β-HSD3-Mediated Cellular AdT to T Conversion

Figure 5A:
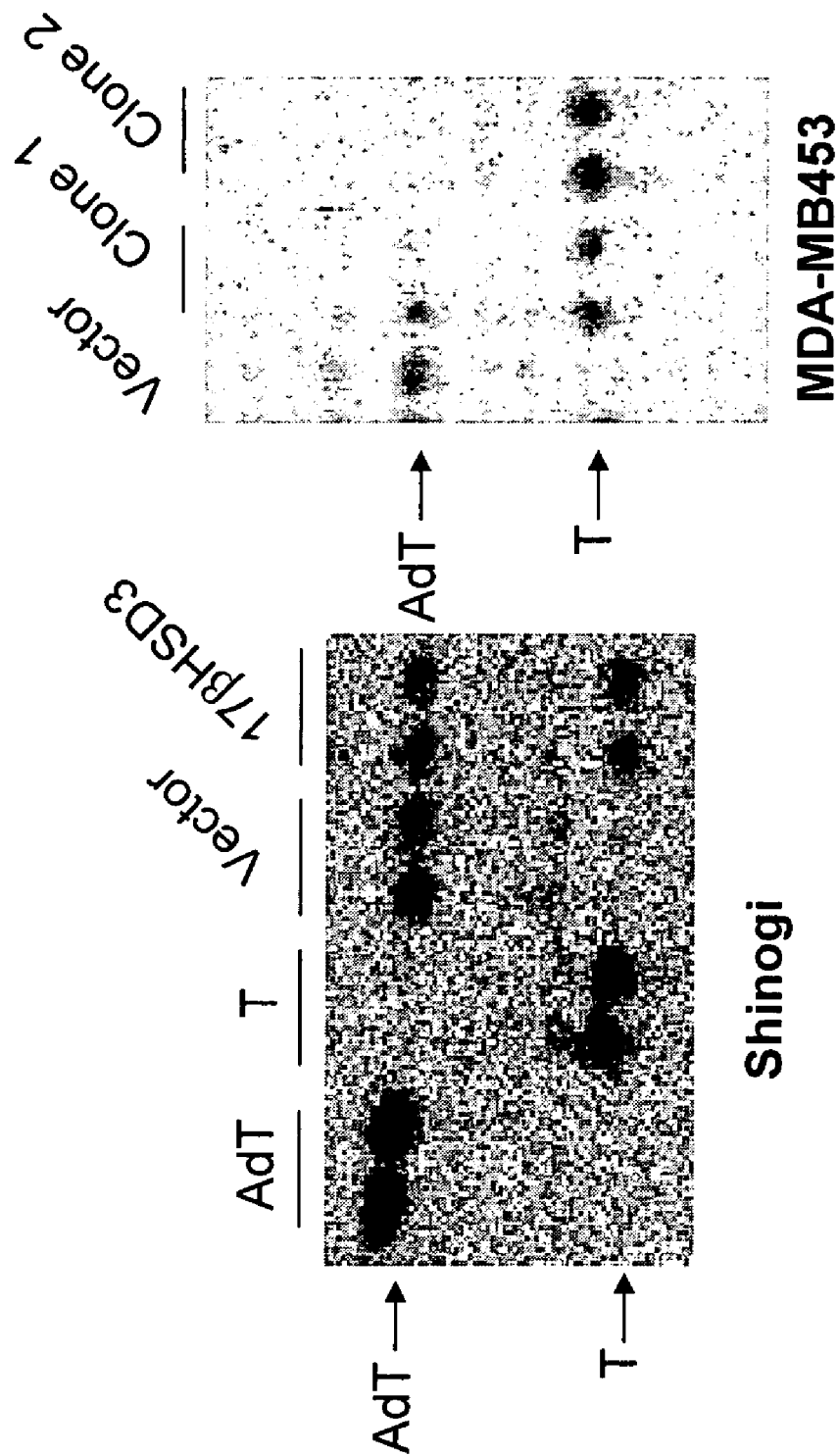
FIG. 5 (FIGS. 5A–5C) illustrates the generation of cell based assays to monitor 17β-HSD3 activity. Shionogi and MDA-MB453 breast cancer cells did not show appreciable AdT to T conversion activity and were used to generate cell stable cell lines of 17β-HSD3 which subsequently displayed pronounced testosterone conversion activity compared to vector transfectants (FIG. 5A). MDA-MB453 cells expressing 17β-HSD3 were used to monitor testosterone-dependent transcription upon androstenedione treatment and the introduction of the androgen-responsive prostate specific antigen (PSA) promoter driving the transcription of secreted alkaline phosphatase (SEAP). The level of 17β-HSD3 mediated testosterone-dependent transcriptional activity compared to vector transfectants is illustrated in FIG. 5B. Inhibition of 17β-HSD3 cell based activity of 1,4-androstadiene-1,6,17-trione and 18β-glycyrrhetinic acid is illustrated in FIG. 5C.

The characterization of breast and prostate tumor cell lines for the 17β-HSD activities enabled the identification of cells which could be engineered for preferred 17β-HSD3 activity to monitor the cellular effects of inhibitors. To this end, Shinogi 115 mouse mammary cells and human MDA-MB453 cells were identified as tumor cells which expressed wild type androgen receptor (AR) but did not display significant androstenedione to testosterone conversion activity. In addition, 17β-HSD mRNA was not detected at appreciable levels in these cells by RT-PCR (data not shown). Stable clonal populations of both cell lines were engineered to stably express human 17β-HSD3 protein. Shinogi-17β-HSD3 and MDA-BM453-17β-HSD3 cells displayed potent androstenedione to testosterone conversion activity compared to vector-transfected cells (FIG. 5A) indicating that observed testosterone conversion is 17β-HSD3 mediated in both of these cells.

Figure 5B:
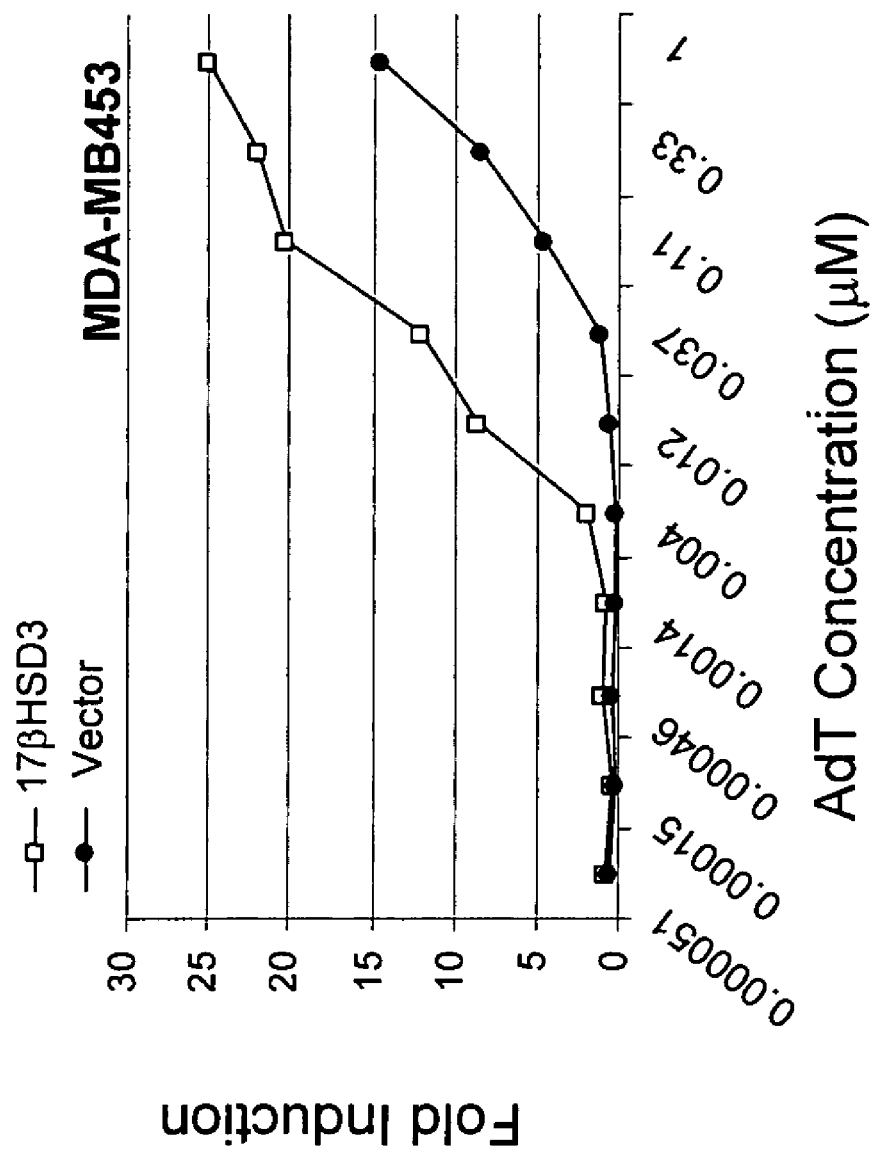

The analysis of 17β-HSD3 steroid conversion by TLC is hampered by the limitation to examine large numbers of compounds. Since both Shinogi-17β-HSD3 and MDA-BM453-17β-HSD3 cells displayed potent AdT to T conversion activity and expressed wild-type AR, it was reasoned that this limitation could be overcome by using an AR based reported assay to monitor the activity of 17β-HSD3. To test this system, a prostate specific antigen (PSA) reporter plasmid was transfected into MDA-MB453 cells stably expressing 17β-HSD3 and stimulated with different concentrations of androstenedione (FIG. 5B). 17β-HSD3-MDA-MB453 cells displayed a potent, dose-response to androstenedione with a 9-fold and 25-fold induction observed at 0.0012 and 1 µM, respectively. A vector-transfectant stable clone also displayed activation of the promoter but only at the higher concentrations of androstenedione consistent with published findings that AR can be activated by high amounts of the precursor. Nonetheless, at 12 nM androstenedione a 9-fold activation was observed in 17β-HSD3-MDA-MB453 transfectants with undetectable activation of vector transfectants indicating that these conditions were robust for the analysis of compounds for effects on 17β-HSD3 cellular activity.

Figure 5C:
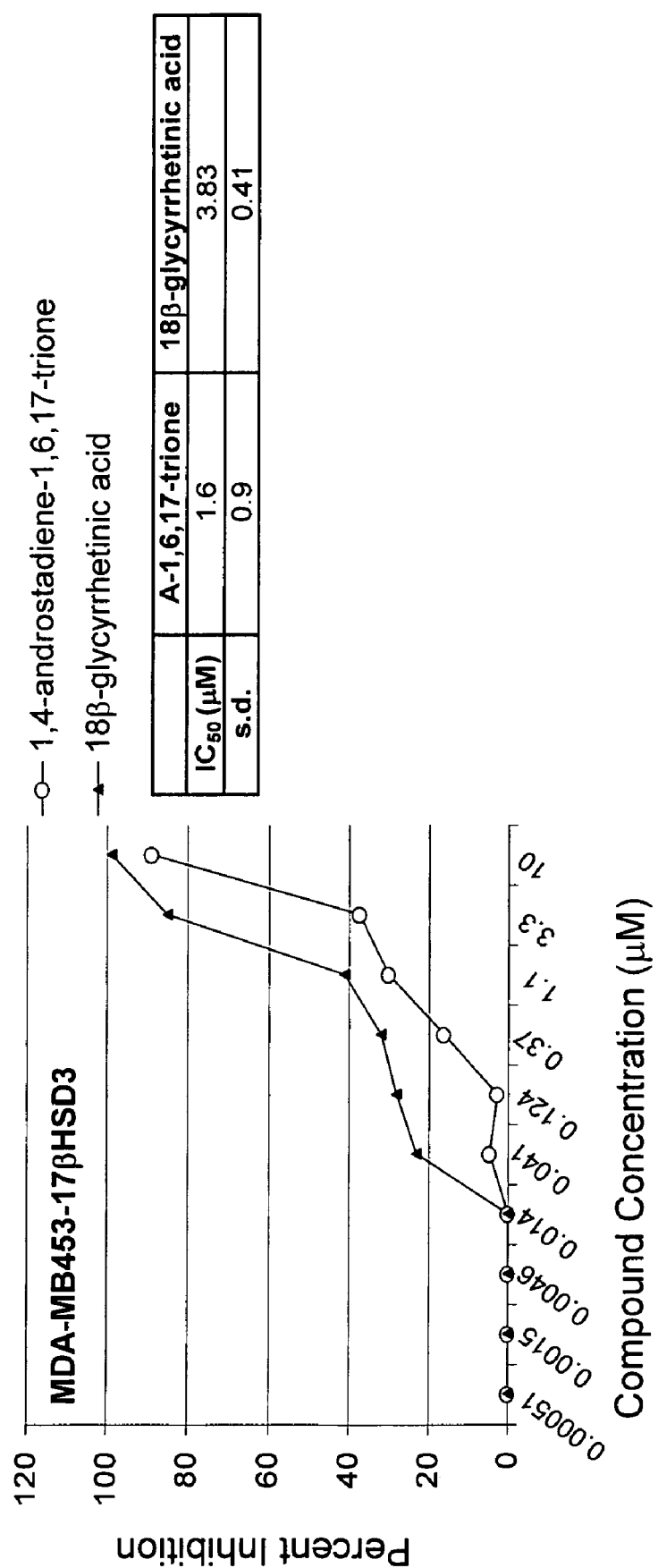

To evaluate the suitability of this cellular assay for monitoring 17β-HSD3 cell based activity, the inhibitory effects of 18β-glycyrrhetinic acid and 1,4-androstadiene-1,6,17-trione were examined. Dose dependent inhibition of 17β-HSD3 cell based activity was observed for both 18β-glycyrrhetinic acid and 1,4-androstadiene-1,6,17-trione with IC50 values of 3.8 and 1.6 µM, respectively (FIG. 5C). No effects were observed for either compound on testosterone-stimulated parental MDA-MB453 indicating that these effects were not mediated through direct effects of these compounds on AR. Taken together, these results indicate the ability to detect low nanomolar inhibition of 17β-HSD3 activity using high throughput biochemical and cell based assays.

Figure 6:
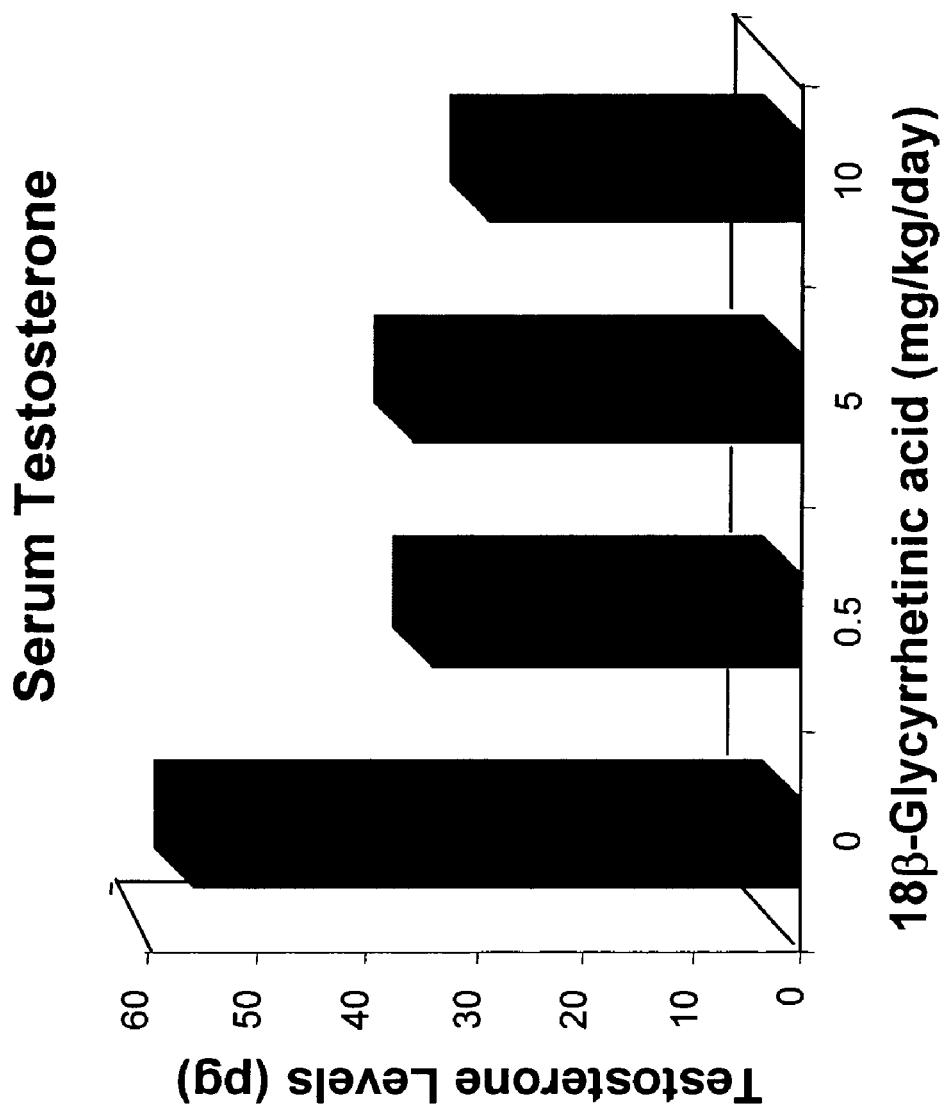
FIG. 6 illustrates the inhibition of testosterone biosynthesis by 18β-glycyrrhetinic acid. Intact rats were administered p.o. the indicated doses of 18β-glycyrrhetinic acid over 14 days and testosterone levels were determined.
Figure 7A:
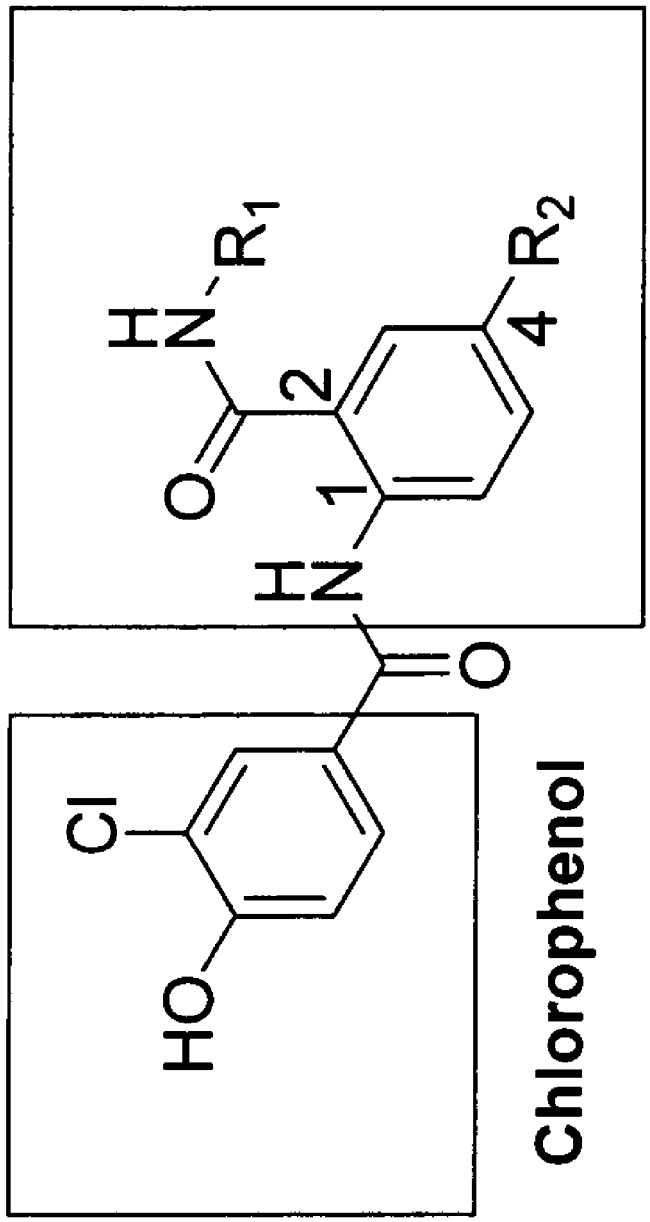
FIG. 7 (FIGS. 7A–7D) illustrates the identification of a novel series of 17β-HSD3 inhibitors. High throughput screening of the 17β-HSD3 biochemical SPA identified a series of anthranilamide compounds represented by the core structure shown in FIG. 7A. Further analysis of this series of compounds revealed a variety of substitutions which affected the biochemical and cell based potency of the compounds (FIG. 7B). This series was exemplified by 2-[(3-chloro-4-hydroxybenzoyl)amino]-N-[2-(2-methoxyphenyl)ethyl]-5-phenoxybenzamide (FIG. 7C), which showed potent inhibitory activity in enzymatic (FIG. 7B) and cell based (FIG. 7D) assays.
Figure 7B:
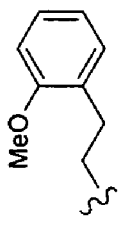
Figure 7B:
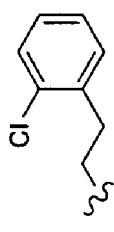
Figure 7B:
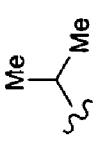
Figure 7B:
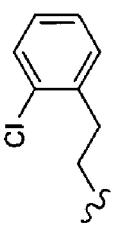
Figure 7B:
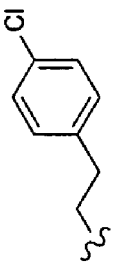
Figure 7C:
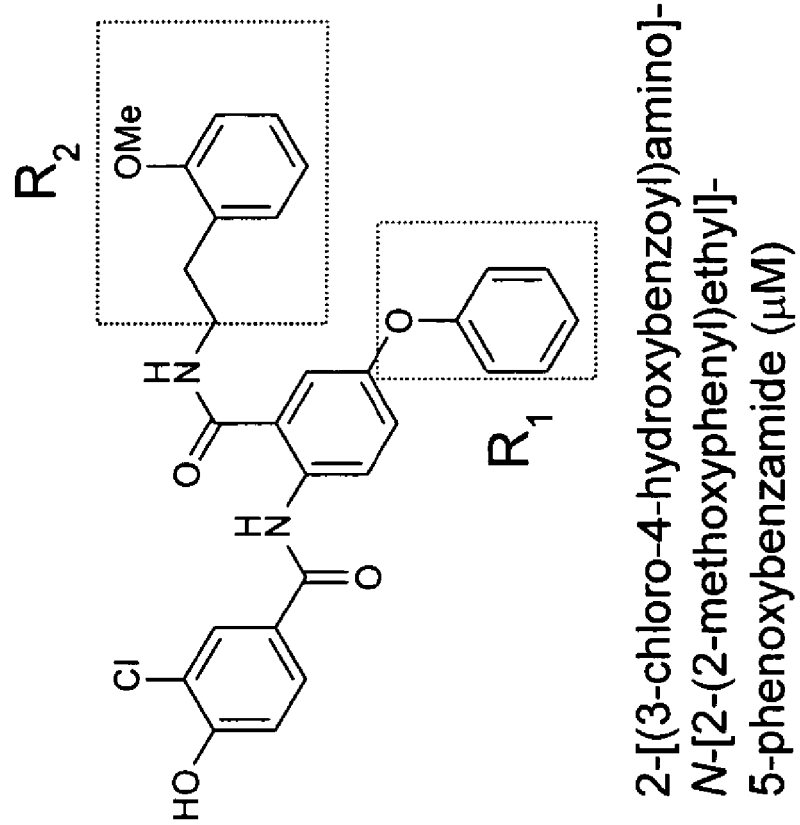
Figure 7D:
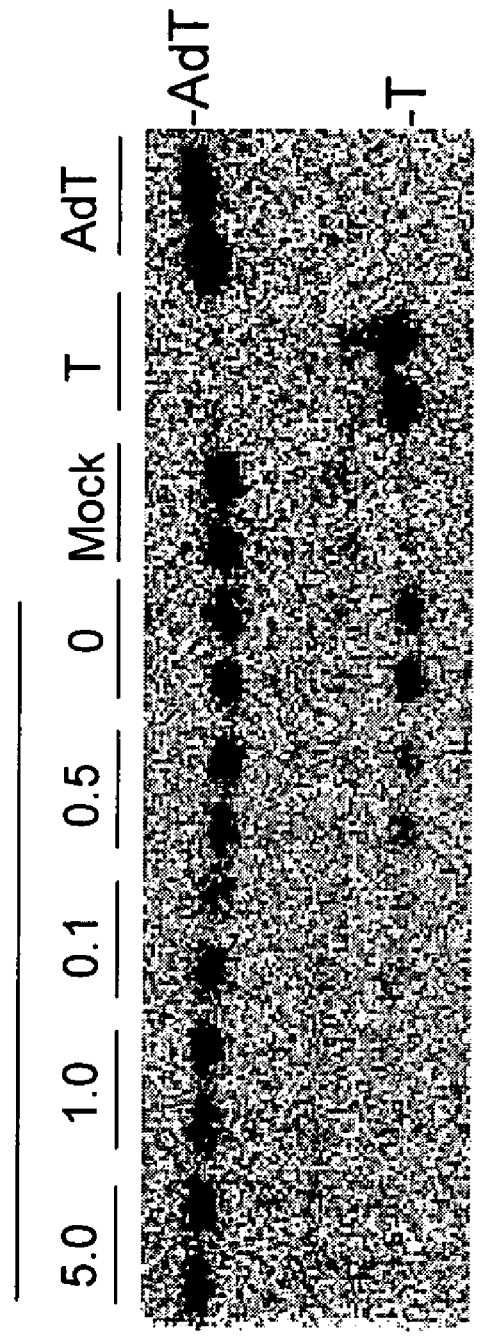

FIG. 6 illustrates the inhibition of testosterone biosynthesis by 18β-glycyrrhetinic acid. Intact rats were administered p.o. the indicated doses of 18β-glycyrrhetinic acid over 14 days and testosterone levels were determined.

Identification of a Novel Series of 17β-HSD3 Inhibitors with Improved Potency

Although 18β-glycyrrhetinic acid and 1,4-androstadiene-1,6,17-trione were identified as inhibitors of 17β-HSD3 biochemical and cell based activity, their potency and pharmacological properties are not optimal. With the development of the described high throughput biochemical and cell based assays, an unbiased screen of compounds was under-taken to identify inhibitors of 17β-HSD3 with improved potency and pharmacological properties. A high throughput screen of >200,000 small molecules was performed using the 17β-HSD3 SPA in a 384 well format. One of the series of compounds identified with potent 17β-HSD3 inhibitory activity was related to the antranilamide class of molecules (FIG. 7). This class of compounds was exemplified by 2-[(3-chloro-4-hydroxybenzoyl)amino]-N-[2-(2-methoxyphenyl)ethyl]-5-phenoxybenzamide which displayed potent inhibition of 17β-HSD3 biochemical and cell based activity with IC50s values of 60 nM and 300 nM, respectively.

To confirm that this class of compounds was inhibiting 17β-HSD3, Shinogi-17β-HSD3 cells incubated with {3H}-androstenedione were analyzed by TLC assay following 2-[(3-chloro-4-hydroxybenzoyl)amino]-N-[2-(2-methoxyphenyl)ethyl]-5-phenoxybenzamide treatment. Similar to what was observed in the cellular 17β-HSD3 PSA reporter assay, an $IC_{50}$ value was estimated for 2-[(3-chloro-4-hydroxybenzoyl)amino]-N-[2-(2-methoxyphenyl)ethyl]-5-phenoxybenzamide at ~300 nM. These results highlight the antranilamide series of molecules represented by 2-[(3-chloro-4-hydroxybenzoyl)amino]-N-[2-(2-methoxyphenyl)ethyl]-5-phenoxybenzamide as novel, potent small molecule inhibitors of 17β-HSD3 activity.

Although the invention has been described in some detail by way of illustration and example for purposes of clarity and understanding, it will be apparent that certain changes and modifications may be practiced within the scope of the appended claims.

What is claimed is:

1. A method for identifying a test agent that inhibits a 17β-hydroxysteroid dehydrogenase 3 (17β-HSD3), said method comprising:
   obtaining a recombinant host cell that expresses said 17β-HSD3 and a testosterone-responsive gene promoter that drives expression of a secreted alkaline phosphatase (SEAP) reporter;
   combining said test agent with said recombinant host cell; and
   measuring the transcription of said SEAP reporter,
   wherein when the amount of said SEAP reporter is lower in the presence of a test agent than in the absence of the test agent, the test agent is identified as an inhibitor of said 17β-HSD3.

2. The method of claim 1, wherein said recombinant host cell is an HEK293 cell.

3. The method of claim 1, wherein said obtaining said recombinant host cell comprises: transfecting said host cell with a polynucleotide comprising a nucleotide sequence that encodes said 17β-HSD3 under conditions such that said host cell produces said 17β-HSD3.

* * * * *

SEQUENCE LISTING

<160> NUMBER OF SEQ ID NOS: 3

<210> SEQ ID NO 1
<211> LENGTH: 1134
<212> TYPE: DNA
<213> ORGANISM: Homo sapiens

<400> SEQUENCE: 1

```
tacacagaga gccacggcca gggctgaaac agtctgttga gtgcagccat ggggacgtc      60 ctgaacagt tcttcatcct cacagggctg ctggtgtgcc tggcctgcct ggcgaagtgc     120
gtgagattct ccagatgtgt tttactgaac tactggaaag ttttgccaaa gtctttcttg    180
cggtcaatgg gacagtgggc agtgatcact ggagcaggcg atggaattgg gaaagcgtac    240
tcgttcgagc tagcaaaacg tggactcaat gttgtcctta ttagccggac gctggaaaaa    300
ctagaggcca ttgccacaga gatcgagcgg actacaggga ggagtgtgaa gattatacaa    360
gcagatttta caaaagatga catctacgag catattaaag aaaaacttgc aggcttagaa    420
attggaattt tagtcaacaa tgtcggaatg cttccaaacc ttctcccaag ccatttcctg    480
aacgcaccgg atgaaatcca gagcctcatc cattgtaaca tcacctccgt agtcaagatg    540
acacagctaa ttctgaaaca tatggaatca aggcagaaag gtctcatcct gaacatttct    600
tctgggatag ccctgtttcc ttggcctctc tactccatgt actcagcttc caaggcgttt    660
gtgtgcgcat tttccaaggc cctgcaagag gaatataaag caaagaagt catcatccag    720 gtgctgaccc catatgctgt ctcgactgca atgacaaagt atctaaatac aaatgtgata    780
accaagactg ctgatgagtt tgtcaaagag tcattgaatt atgtcacaat tggaggtgaa    840
acctgtggct gccttgccca tgaaatcttg gcgggctttc tgagcctgat cccggcctgg    900
gccttctaca gcggtgcctt ccaaaggctg ctcctgacac actatgtggc atacctgaag    960
ctcaacacca aggtcaggta gccaggcggt gaggagtcca gcacaaacctt ttcctcacca   1020 gtcccatgct ggctgaagag gaccagagga gcagaccagc acttcaacct agtccgctga   1080
agatggaggg ggctggggtc acagaggcat agaatacaca ttttttgcca cttt          1134
```

<210> SEQ ID NO 2
<211> LENGTH: 310
<212> TYPE: PRT
<213> ORGANISM: Homo sapiens

<400> SEQUENCE: 2

| | | | | | | | | | | | | | | |
|---|---|---|---|---|---|---|---|---|---|---|---|---|---|---|
|Met|Gly|Asp|Val|Leu|Glu|Gln|Phe|Phe|Ile|Leu|Thr|Gly|Leu|Leu|Val
1| | | |5| | | | |10| | | | |15| |

Cys Leu Ala Cys Leu Ala Lys Cys Val Arg Phe Ser Arg Cys Val Leu
            20              25              30

Leu Asn Tyr Trp Lys Val Leu Pro Lys Ser Phe Leu Arg Ser Met Gly
        35              40              45

Gln Trp Ala Val Ile Thr Gly Ala Gly Asp Gly Ile Gly Lys Ala Tyr
    50              55              60

Ser Phe Glu Leu Ala Lys Arg Gly Leu Asn Val Val Leu Ile Ser Arg
65            70              75            80

Thr Leu Glu Lys Leu Glu Ala Ile Ala Thr Glu Ile Glu Arg Thr Thr
            85              90              95

Gly Arg Ser Val Lys Ile Ile Gln Ala Asp Phe Thr Lys Asp Asp Ile
        100             105            110

Tyr Glu His Ile Lys Glu Lys Leu Ala Gly Leu Glu Ile Gly Ile Leu
        115             120            125

Val Asn Asn Val Gly Met Leu Pro Asn Leu Leu Pro Ser His Phe Leu
130             135            140

Asn Ala Pro Asp Glu Ile Gln Ser Leu Ile His Cys Asn Ile Thr Ser
145            150             155            160

Val Val Lys Met Thr Gln Leu Ile Leu Lys His Met Glu Ser Arg Gln
        165             170            175

Lys Gly Leu Ile Leu Asn Ile Ser Ser Gly Ile Ala Leu Phe Pro Trp
        180             185            190

Pro Leu Tyr Ser Met Tyr Ser Ala Ser Lys Ala Phe Val Cys Ala Phe
        195             200            205

Ser Lys Ala Leu Gln Glu Glu Tyr Lys Ala Lys Glu Val Ile Ile Gln
210             215            220

Val Leu Thr Pro Tyr Ala Val Ser Thr Ala Met Thr Lys Tyr Leu Asn
225            230              235            240

Thr Asn Val Ile Thr Lys Thr Ala Asp Glu Phe Val Lys Glu Ser Leu
        245             250            255

Asn Tyr Val Thr Ile Gly Gly Glu Thr Cys Gly Cys Leu Ala His Glu
        260             265            270

Ile Leu Ala Gly Phe Leu Ser Leu Ile Pro Ala Trp Ala Phe Tyr Ser
        275             280            285

Gly Ala Phe Gln Arg Leu Leu Leu Thr His Tyr Val Ala Tyr Leu Lys
        290             295            300

Leu Asn Thr Lys Val Arg
305             310

<210> SEQ ID NO 3
<211> LENGTH: 548
<212> TYPE: DNA
<213> ORGANISM: Homo sapiens

<400> SEQUENCE: 3

```
gatcttttta tgatgacagt agcaatgtat ctgtggagct ggattctggg ttgggagtgc      60
aaggaaaaga atgtactaaa tgccaagaca tctatttcag gagcatgagg aataaaagtt     120
ctagtttctg gtctcagagt ggtgcaggga tcagggagtc tcacaatctc ctgagtgctg     180
gtgtcttagg gcacactggg tcttggagtg caaaggatct aggcacgtga ggcttttgtat    240 gaagaatcgg ggatcgtacc cacccccctgt ttctgtttca tcctgggcat gtctcctctg   300
```

```
cctttgtccc ctagatgaag tctccatgag ctacaagggc ctggtgcatc cagggtgatc      360
tagtaattgc agaacagcaa gtgctagctc tccctcccct tccacagctc tgggtgtggg      420
aggggtttgt ccagcctcca gcagcatggg gagggccttg gtcagcctct gggtgccagc      480
agggcagggg cggagtcctg gggaatgaag gtttttatagg gctcctgggg gaggctcccc     540
agcccccaa                                                              548
```